United States Patent [19]

Lentz et al.

[11] Patent Number: 4,831,236
[45] Date of Patent: May 16, 1989

[54] APPARATUS FOR CLEARING A CELLULOSE ESTER FILTER

[75] Inventors: Henry P. Lentz, Pittsburgh; Larry R. Delaney, Cheswick; Charles J. Matone, Jr., Greensburg; Richard J. Lee, Murrysville, all of Pa.; Dan H. Lang, LaJolla, Calif.

[73] Assignee: RJ Lee Group, Inc., Monroeville, Pa.

[21] Appl. No.: 96,726

[22] Filed: Sep. 14, 1987

[51] Int. Cl.⁴ .............................................. H05B 3/42
[52] U.S. Cl. ................................... 219/271; 219/273; 219/275
[58] Field of Search ............... 219/271, 390, 272, 273, 219/274, 275, 276, 303, 304, 214; 261/DIG. 65

[56] References Cited

U.S. PATENT DOCUMENTS

| | | | |
|---|---|---|---|
| 1,162,537 | 11/1915 | Yager | 219/304 |
| 1,293,896 | 2/1919 | Paasche | 219/303 |
| 2,307,924 | 1/1943 | Gillespie | 219/304 |
| 2,467,393 | 4/1949 | Leher | 219/272 |
| 2,481,813 | 9/1949 | Bede | 219/303 |
| 2,878,360 | 3/1959 | Tavender | 219/304 |
| 3,215,416 | 11/1965 | Liben | 219/272 |
| 4,027,786 | 6/1977 | Ryckman | 219/303 |
| 4,260,873 | 4/1981 | Simmonds | 219/275 |
| 4,414,037 | 11/1983 | Friedheim | 219/275 |
| 4,465,922 | 8/1984 | Kolibas | 219/304 |

OTHER PUBLICATIONS

"An Asbestos Sample Filter Clearing Procedure", Paul A. Baron & Gregory Pickford, National Institute for Occupational Safety and Health, 4676 Columbia Parkway, Cincinnati, Ohio 45226.

Primary Examiner—Teresa J. Walberg
Attorney, Agent, or Firm—Webb, Burden, Ziesenheim & Webb

[57] ABSTRACT

An apparatus for acetone clearing of cellulose or nitrate membrane filters includes an elongated electric heater element with tubing for transporting acetone coiled around said heater element and in contact therewith. Liquid acetone is introduced to said tubing wherein it is heated by said heater element and acetone vapor is discharged from said tubing. The temperature of the coiled tubing is thermostatically controlled. Acetone vapor is removed from said tubing and passed over a glass slide having an exposed filter containing particulars, such as asbestos fibers. The vapors clear the filter to render it translucent for examination in optical microscopy.

10 Claims, 1 Drawing Sheet

APPARATUS FOR CLEARING A CELLULOSE ESTER FILTER

BACKGROUND OF THE INVENTION

This invention relates to a compact slide clearing apparatus for use with phase contrast microscopy.

More particularly, this invention relates to an apparatus for clearing a filter, such as a filter containing asbestos fibers or other particulates. The apparatus is used to clear a cellulose ester or nitrate membrane filter with acetone vapors. In the apparatus a small amount of liquid acetone is rapidly vaporized and ducted to the filter to provide even and rapid clearing of the filter to render it translucent during subsequent optical microscopy.

The apparatus of the invention is employed as an element in a method which is particularly useful for analyzing filter sample concentrations for asbestos fibers. The analyzing method involves chemically collapsing the cellulose ester or nitrate filter with a stream of acetone vapor to provide a clear background against which to count the individual fibers with an optical microscope.

To clear an individual filter sample about 0.2 ml of liquid acetone is injected into the apparatus. The liquid flows downwardly through the aparatus wherein it is vaporized. The vapor is ejected through a nozzle and is condensed on the filter which is located on a glass slide. The condensation is rapid. The entire injection and clearing process takes no more than about 5 onds.

A glass slide carrying a one-fourth pie-shaped segment of a 25 mm filter can be positioned on a galss slide holder in the apparatus. The apparatus is preheated and 0.2 ml liquid acetone can be loaded into the apparatus by pipette or syringe. The amount of acetone will depend on the size of the filter element with the amount increasing with an increase in the size of the filter element. The apparatus will vaporize the acetone at a temperature in the range of about 155° to 165° F. and then eject the acetone vapor over the slide. The entire clearing operation will occur within about 5 seconds following which the slide is immediately removed. If the slide is subjected to the heat of the apparatus for a longer time period it can curl up and the cleared filter can become distorted. The amount of acetone used should be kept to a minimum because acetone can constitute a fire hazard.

If the apparatus is operated at temperatures above the range 155° to 165° F. the acetone may boil violently, causing liquid droplets to reach the surface of the filter. Also, at higher temperatures the acetone may tend to decompose. At lower operating temperatures, the acetone may stay on the filter and slide for an unduly long time period allowing the surface tension of the liquid to draw dissolved filter material and particles away from the edge of the filter.

In the analyzing method, the cleared filter on the slide is then covered with triacetin and a cover slip. About a ten minute wait allows maximum clearing of the filter surface. The slide is then ready for examination with an optical microscope.

SUMMARY OF THE INVENTION

The apparatus of this invention comprises an elongated electric heater cartridge element in combination with tubing for transporting acetone. The tubing is coiled around and in contact with the heater element. The heater-coiled tubing combination can be embedded in a heat conductive cement, such as solder, to enhance the rate of heat transfer between the heater element and the coiled tubing. The inlet end of the tubing comprises a mouth for receiving liquid acetone. The mouth can be provided with barrier means, such as a rubber septum, for preventing escape of acetone vapors. The outlet end of the tube is widened to comprise a discharge nozzle for removing acetone vapor. Slide supporting means is disposed below the nozzle to receive vapors from said discharge nozzle and for exposing the slide to said vapors. The slide supporting means can contain an absorbent for acetone, such as charcoal.

The heater cartridge is connected in series with an electric power source, an on-off switch, an automatic thermostat switch and a manual reset temperature overheat switch. An electric indicator light is shunted across the thermostat switch. When the desired temperature range is achieved, the thermostat switch opens to shut off the heater and the indicator lights up to signal temperature readiness of the apparatus. The signal light goes off when the thermostat switch is closed, indicating that the apparatus is being heated to the desired temperature but is not yet temperature ready. Acetone is injected when the temperature readiness condition is achieved.

BRIEF DESCRIPTION OF THE DRAWINGS

The apparatus will be more completely understood by reference to the following drawings in which.

DESCRIPTION OF THE PREFERRED EMBODIMENT

Figure 1:
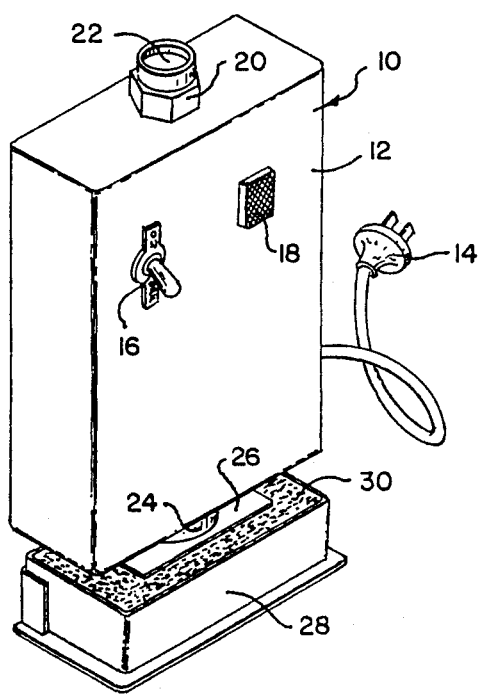
FIG. 1 is an exterior view showing the housing of the compact apparatus of the invention.

Referring to FIG. 1, clearing apparatus 10 includes housing 12, which can be plastic or metallic, such as aluminum, from which electric plug 14 extends to a power source, not shown. On-off switch 16 controls the flow of electric power to the apparatus and electric light signal 18 indicates the temperature readiness of the apparatus. Mouth 20 provides access for liquid acetone to the apparatus and rubber septum barrier 22 within mouth 20 prevents egress of acetone from mouth 20.

Acetone vapor is emitted through nozzle 24 to glass slide plate 26. Slide plate 26 is disposed on slide support means 28 which contains an acetone absorbent, such as charcoal bed 30. Slide support means 28 is connected to housing 12 by means of a flexible rear brace, not shown.

Figure 2:
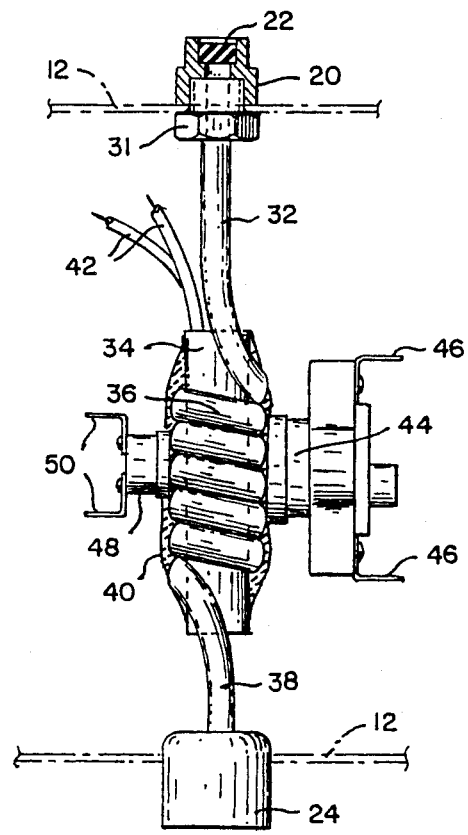
FIG. 2 is a view of the apparatus with the housing removed.

FIG. 2 shows mouth 20 containing rubber septum 22 secured to the top panel of casing 12 by means of nut 31. Copper tubing inlet zone 32 descends vertically from mouth 20 to vertically disposed electric cylindrical heater cartridge 34 and the tubing is tightly coiled around cartridge 34, as shown at zone 36. Copper tubing discharge zone 38 descends vertically from tubing coil 36 to discharge expander nozzle 24. A layer of thermally conductive cement 40, such as a metal alloy solder, embeds both tubing coil 36 and cartridge 34 to improve heat transfer between heater 34 and coil 36.

A pair of electric leads 42 extends from heater cartridge 34 to plug 14 to supply electric power to cartridge 34. A thermostat 44 having a bimetallic disk, not shown, on the outer surface of coil 36 is provided with a pair of wire leads 46. Thermostat 44 can maintain a coil temperature within the temperature range 155° to 165° F. Manual reset fail safe breaker switch 48 is provided with a temperature sensitive means, not shown, disposed on the surface of tubing coil 36, and has a pair of electric wire leads 50. Breaker switch 48 can be set to open at a temperature 250° F., which temperature can occur upon a failure of thermostat 44.

Figure 3:
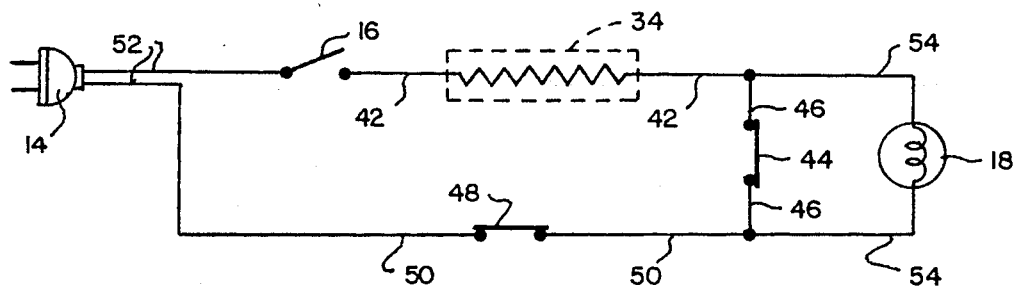
FIG. 3 is a diagram of the electric circuit employed by the apparatus.

FIG. 3 illustrates the electric circuitry of the apparatus. Electric power from plug 14 is supplied to the circuit throught wires 52. The circuit includes manual on-off switch 16 which is connected in series with heater cartridge 34 by wires 42. Cartridge 34 is connected in series with thermostat switch 44 by wires 46. Switch 44 is connected in series with temperature overheat manual reset breaker switch 48 by wires 50. Shunt wires 54 connect temperature ready signal indicator light 18 across thermostat switch 44.

Thermostat switch 44 is closed during the heating period. When switch 44 is closed, no current flows through signal light 18 and signal light 18 is off. Switch 44 is open when the temperature at coil 34 is within the range 155° to 165° F. When switch 44 is open, some current flows through signal light 18 and signal light 18 goes on when the temperature is between 155° and 165° F. and switch 44 is open. Breaker switch 48 opens if the temperature inadvertently reaches 250° F., and then must be manually reset.

Liquid acetone can be injected through rubber septum 22 by means of a needle with a syringe to supply liquid acetone to tubing coil 36 where it is vaporized at a temperature in the range 155° to 165° F. Acetone vapor is discharged through expander nozzle 24 to slide 26 on which a wedge of filter, not shown, is placed. Excess acetone from expander nozzle 24 is absorbed by charcoal bed 30.

The figures show that all electrical connections and hot surfaces are contained within housing 12. By employing a flexible brace to connect housing 12 with slide support means 28, slide 26 can be positioned closer or farther from vapor nozzle 24, as desired. Fail-safe switch 48 prevents a temperature runaway in the event of thermostat failure. Charcoal bed 30 absorbs all excess vapors, so that no exhaust hood is required. The apparatus can employ a 150 watt heater element, requiring a preheat time of only about 1 minute. When light 18 is lit, preheat is complete and the unit is ready for opeation. The coil can comprise ¼ inch copper tubing. Septum 22 prevents blowback of vapor. If desired, septum 22 can be omitted and acetone can be introduced with a pipette, with the pipette remaining in place in mouth 20 to prevent blow-back of vapor.

We claim:

1. An apparatus for acetone clearing of cellulose ester or nitrate membrane filters and the like comprising:

tubing for transport of acetone, said tubing having an upper inlet end, a lower discharge and an intermediate coiled section communicating therebetween; an elongated heater element with temperature control means for controlling a temperature thereof, said heater element positioned within and in contact with the coiled section of the tubing;

inlet opening means at said tubing inlet end including means for introducing a measured volume of liquid acetone to said tubing and means for closing-off the inlet end after said acetone is introduced;

said coiled section of the tubing adapted to receive the measured volume of liquid acetone by gravity flow from the inlet opening means and wherein said measured volume of liquid acetone is heated and converted to a vapor phase of a measured volume, said tubing discharge end adapted to receive the acetone vapor from the coiled section and to emit said vapor as a measured volume therefrom; and slide supporting means in a position spaced beneath the discharge end of the tubing adapted to support a prepared slide carrying a filter to be treated thereon and adapted to receive the measured volume of acetone vapor emitted from said tubing discharge end.

2. The apparatus of claim 1 including thermally conductive cement embedding said coiled tubing and said heater element.

3. The apparatus of claim 1 wherein said elongated heater element and said tubing are vertically disposed.

4. The apparatus of claim 1 including housing means for enclosing said apparatus.

5. The apparatus of claim 1 including a glass slide on said slide supporting means, said glass slide supporting a filter containing asbestos fibers.

6. The apparatus of claim 1 wherein said inlet opening means includes barrier means for penetration by a syringe needle whereby, in use, a measured volume of liquid acetone is introduced into said tubing inlet end.

7. The apparatus of claim 1 wherein the slide supporting means includes a support surface of acetone absorbing material.

8. The apparatus of claim 7 wherein the acetone absorbing material is charcoal.

9. The apparatus of claim 1 wherein the temperature control means is adapted to control a temperature within the coiled section between about 155° F. to about 165° F.

10. The apparatus of claim 1 wherein the heater element is adapted to be connected with an electrical power source and including thermostat switch means and temperature overheat switch means, said apparatus including electric indicator means to signal temperature readiness of said apparatus when said thermostat switch means is in an open position.

* * * * *

UNITED STATES PATENT AND TRADEMARK OFFICE
CERTIFICATE OF CORRECTION

PATENT NO. : 4,831,236

DATED : May 16, 1989

INVENTOR(S) : Henry P. Lentz, Larry R. Delaney, Charles J. Matone, Jr., Richard J. Lee and Dan H. Lang It is certified that error appears in the above-identified patent and that said Letters Patent is hereby corrected as shown below:

In the Abstract Lines 10-11 "particulars" should read --particulates--.

Column 1 Line 31 "onds" should read --seconds--.

Column 1 Line 33 "galss" should read --glass--.

Column 3 Line 8 after "temperature" (first occurrence) insert --of--.

Column 3 Line 12 "throught" should read --through--.

Column 3 Line 48 "opeation" should read --operation--.

Claim 6 Column 4 Line 38 before "barrier" insert --rubber septum--.

Signed and Sealed this

Sixteenth Day of January, 1990

*Attest:*

JEFFREY M. SAMUELS

*Attesting Officer*     Acting Commissioner of Patents and Trademarks